United States Patent [19]

Masters

[11] Patent Number: 4,669,484
[45] Date of Patent: Jun. 2, 1987

[54] AUTOMATIC LEVELING DEVICE FOR HEMODYNAMIC PRESSURE MEASURING SYSTEM

[76] Inventor: Thomas N. Masters, 518 Hermitage Ct., Charlotte, N.C. 28207

[21] Appl. No.: 910,122

[22] Filed: Sep. 22, 1986

[51] Int. Cl.⁴ ............................................. A61B 5/02
[52] U.S. Cl. .................... 128/673; 128/674; 33/367
[58] Field of Search ............... 128/672–675, 128/748; 33/367, 381, 383

[56] References Cited

U.S. PATENT DOCUMENTS

| | | | |
|---|---|---|---|
| 3,495,585 | 2/1970 | Halligan et al. | 128/674 |
| 3,590,809 | 7/1971 | London | 128/674 |
| 3,590,818 | 7/1971 | Lemole | 128/674 |
| 3,602,214 | 8/1971 | London et al. | 128/674 |
| 3,636,942 | 1/1972 | Nye | 128/674 |
| 3,690,312 | 9/1972 | Leibinsohn | 128/674 |
| 3,693,612 | 9/1972 | Donahoe et al. | 128/674 |
| 3,996,927 | 12/1976 | Frank | 128/675 |
| 4,026,156 | 5/1977 | Bowditch et al. | 33/367 X |
| 4,135,509 | 1/1979 | Shannon | 128/674 |
| 4,231,163 | 11/1980 | Turloff | 33/367 |
| 4,431,009 | 2/1984 | Marino, Jr. et al. | 128/674 X |
| 4,489,454 | 12/1984 | Thompson | 5/503 |
| 4,546,774 | 10/1985 | Haught | 128/673 |

OTHER PUBLICATIONS

Blackburn et al., "A Self-Levelling Central Venous Electromanometer", *Med. and Biol. Eng.*, vol. 12, No. 3, 5–1974.

*Primary Examiner*—Kyle L. Howell
*Assistant Examiner*—Angela D. Sykes
*Attorney, Agent, or Firm*—Bell, Seltzer, Park & Gibson

[57] ABSTRACT

The present leveling device is operable with a hemodynamic pressure measuring system which includes a pressure catheter to be implanted in the body of the patient and pressure measuring device connected by a tube to the catheter and supported on a vertically movable support platform. The present automatic leveling device operates to automatically maintain the pressure measuring device at the same level as the catheter implanted in the patient and includes a tube level with one end being connected to the patient and at the same level as the catheter implanted in the patient and with the other end being connected to the vertically movable support for the pressure measuring device. A sensor is associated with the tube level and is operable in response to vertical movement of the catheter implanted in the patient to automatically raise and lower the vertically movable support for the pressure measuring device in response to vertical movement of the catheter implanted in the patient.

9 Claims, 3 Drawing Figures

4,669,484

AUTOMATIC LEVELING DEVICE FOR HEMODYNAMIC PRESSURE MEASURING SYSTEM

FIELD OF THE INVENTION

This invention relates generally to a hemodynamic pressure measuring system for accurately monitoring the pressure of blood or other fluids in the body of a patient, and more particularly to an automatic leveling device for imparting vertical movement to the pressure measuring device so as to automatically maintain the pressure measuring device at the same level as the catheter implanted in the patient and being operable in response to corresponding vertical movement of the catheter.

BACKGROUND OF THE INVENTION

Manometer and transducer type systems are widely used for measuring and monitoring hemodynamic pressure in the body of a patient and these devices include a pressure catheter adapted to be implanted in a particular location in the body of the patient, usually in the right atrium of the heart. The catheter is connected to the pressure measuring device by a tube containing pressure-transmitting fluid and the pressure measuring device is supported for vertical adjustment adjacent the patient. It is well known that the pressure measuring device must be maintained at the same vertical level as the catheter in order to obtain accurate pressure measurements.

When the pressure measuring and monitoring system is initially connected to the patient, it is necessary to vertically adjust the level of the pressure measuring device so that it is positioned at the same level as the catheter implanted in the patient. When the patient changes position, for example when the bed is raised or lowered or when the patient moves between reclining and inclined positions, the vertical position of the implanted catheter also changes vertical positions and the pressure measuring device must also be correspondingly raised or lowered to be positioned at the same level as the catheter, in order to continue to accurately measure and monitor the hemodynamic pressure in the body of the patient. Thus, any adjustment in the vertical position of the patient requires that an attendant make a manual vertical adjustment of the pressure measuring device to a corresponding up or down position to insure a continuous accurate pressure reading.

The necessity to maintain the pressure measuring device at the same level as the catheter has long been recognized and various devices have been proposed for manually aligning the pressure measuring device at the same level as the catheter. For example, U.S. Pat. Nos. 3,495,585; 3,590,818; 3,602,214; 3,690,312; 3,636,942; 3,693,612; 3,996,927; 4,135,509; and 4,431,009 disclose devices used to aid the attendant in vertically aligning the pressure measuring device at the same level as the catheter implanted in the patient. However, the devices shown in these prior patents still require that an attendant make a manual adjustment each and every time that the position of the patient is changed and the vertical level of the implanted catheter is changed.

U.S. Pat. No. 4,489,454 also recognizes the importance of maintaining the level of the pressure measuring device, in this case a transducer, at the same level as the heart of the patient in order to obtain accurate readings. This patent attempts to solve this problem by mounting the transducer on the bed so that changes in the vertical position of the bed also raise and lower the vertical level of the transducer. However, the device of this patent must still be manually adjusted when initially connected to the patient so as to be in vertical alignment with the heart of the patient and provides no means for changing the vertical position of the transducer when the position of the patient changes relative to the level of the bed.

SUMMARY OF THE INVENTION

With the foregoing in mind, it is an object of the present invention to provide an automatic leveling device for a hemodynamic pressure measuring system for automatically aligning and maintaining the pressure measuring device at the same level as the catheter and in response to corresponding vertical movement of the patient with the catheter implanted therein.

The automatic leveling device of the present invention includes a liquid level tube connected at one end to the patient and at the same level as the catheter implanted in the patient and with the other end being connected to a vertically movable support for the pressure measuring device, illustrated as a transducer. Sensor means is associated with the end of the liquid level tube adjacent the transducer and is operable to detect vertical movement of the liquid level in the tube in response to vertical movement of the patient with the catheter implanted therein, either above or below a predetermined alignment level. Motive means is provided for automatically raising and lowering the support for the transducer and in response to the sensor indicating a corresponding vertical movement of the catheter implanted in the patient so that the pressure measuring transducer is maintained at the same level as the catheter implanted in the patient.

In accordance with the present invention, the liquid level tube of the automatic leveling device contains an electroconductive material, such as mercury. The sensor means includes spaced-apart electrodes positioned in the end of the tube fixed on the vertically movable support for the transducer so that the level of the mercury in the leveling tube contacts the electrodes and operates a reversible motor which is drivingly connected to a vertical threaded shaft supporting the table or platform on which the transducer is fixed. Rotation of the reversible motor in one direction causes the threaded support post to rotate and raise the support table while reverse rotation of the motor causes the threaded support rod to rotate in the opposite direction and thereby lower the transducer support table.

BRIEF DESCRIPTION OF THE DRAWINGS

Other objects and advantages will appear as the description proceeds when taken in connection with the accompanying drawings, in which.

DESCRIPTION OF THE ILLUSTRATED EMBODIMENT

Figure 2:
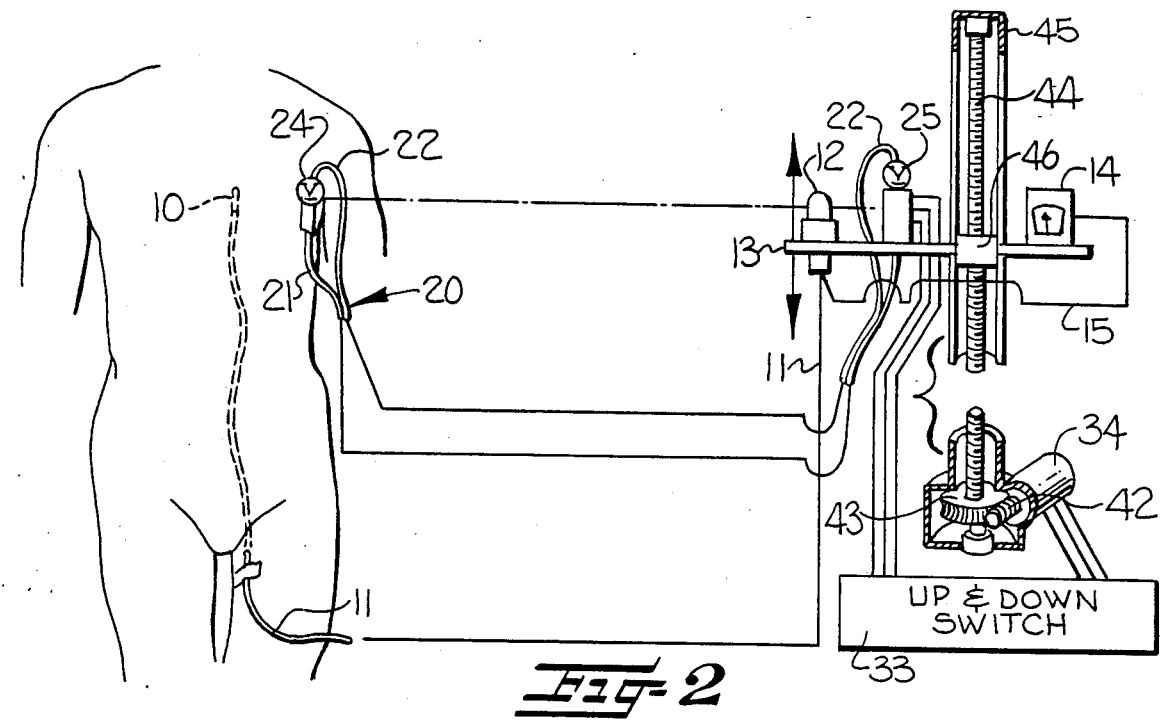
FIG. 2 is a schematic diagram of the automatic leveling device connected to the patient and with parts in section to illustrate the manner in which up and down vertical movement is automatically imparted to the transducer support table in accordance with the present invention.

The present automatic leveling device is illustrated in association with a transducer type of hemodynamic pressure measuring device. However, it is to be understood that the present automatic leveling device can also be used in association with a manometer type of hemodynamic pressure measuring system. The hemodynamic pressure measuring and monitoring apparatus illustrated in the drawings includes a pressure catheter, indicated in dotted lines at 10 in FIG. 2, and being of the type adapted to be implanted in a particular location in the body of the patient. As shown in the drawings, the pressure catheter 10 is implanted in the heart of the patient and is attached to one end of a tube 11 containing pressure-transmitting fluid. The tube 11 is illustrated as being threaded into a vein in the groin of the patient and extends to the heart where the catheter 10 is implanted, usually in the right atrium.

The other end of the pressure-transmitting tube 11 is connected to pressure measuring means, illustrated as a transducer 12, fixed on a table or platform 13 supported for vertical movement. The transducer 12 is connected to and operates a suitable pressure indicating and monitoring device 14 by suitable wires 15. The monitoring and indicating device 14 may be a simple gauge to indicate the pressure detected by the catheter 10 or it may be an electronic monitor which records the blood pressure measurements. The transducer 12 may be connected to a central computer, not shown, for patient monitoring purposes.

The hemodynamic pressure measuring and monitoring apparatus thus far described is of the general type heretofore employed and the support table or platform 13 is normally supported on some type of stand for manual vertical adjustment by the attendant to initially align the transducer 12 vertically with the position of the catheter 10. Also, this conventional type device requires that the attendant vertically adjust the position of the table or platform 13 when the vertical position of the patient changes so as to maintain the transducer 12 at the same vertical level as the catheter 10.

Figure 3:
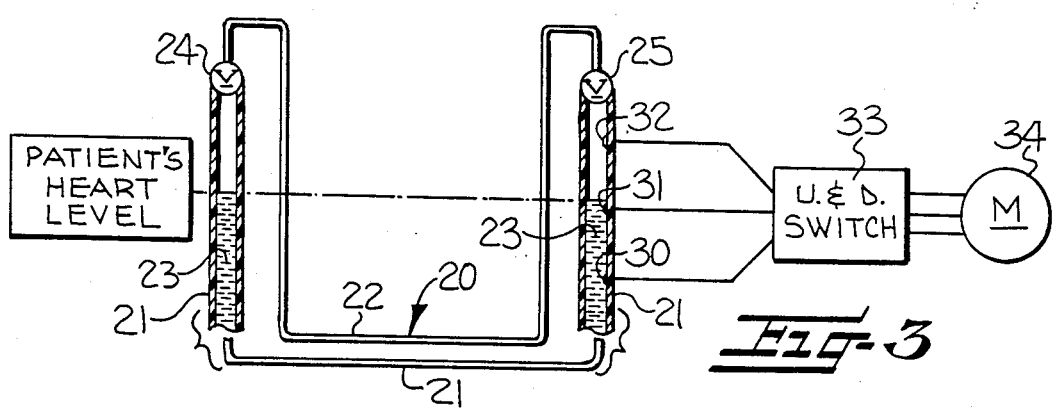
FIG. 3 is a schematic diagram illustrating the manner in which the liquid level tube is utilized to control the operation of the automatic leveling device.

In accordance with the present invention, the table or platform 13 is automatically raised and lowered to maintain the transducer 12 at the same vertical level as the catheter 10 and includes liquid level tube means, broadly indicated at 20. The liquid level tube means 20 preferably includes two tubes 21, 22 which may be integrally joined in the medial portion thereof. The tube 21 contains a liquid, such as electrically conductive mercury indicated at 23 in FIG. 3, maintaining a predetermined level at opposite end portions, in accordance with the vertical positions of the opposite end portions. The tube 22 contains air and is connected at opposite ends to the opposite ends of the liquid-containing tube 21 by means of filter valves 24, 25 so that air can freely flow into and out of the upper ends of the liquid-containing tube 21 as the mercury level therein is changed. The filter valves 24, 25 permit the passage of air therethrough but prevent the passage of the mercury out of either end of the liquid tube 21.

Means is provided for connecting one end portion of the tube 21 to the patient at the same level as the catheter 10 implanted in the patient. Any suitable means may be provided for connecting the end portion of the tube 21 to the patient, such as adhesive tape, a vacuum cup or the like. Suitable means is also provided for connecting the opposite end of the tube 21 to the vertically movable platform or table 13 so that this end of the tube 21 is raised and lowered with the table 13 and with the transducer 12 fixed thereto.

Sensor means is associated with the end of the tube means 21 supported on the vertically movable table 13 and is operable to sense and signal vertical movement of the mercury level in the tube 21 in response to vertical movement of the catheter 10 implanted in the patient above and below a predetermined level. The sensor means illustrated in the drawings includes vertically spaced electrodes 30, 31 and 32 positioned inside of the end portion of the tube 21 and connected by suitable wires to an up and down switch 33 which forms a part of motive means for automatically raising and lowering the table 13 in response to vertical movement of the catheter 10 implanted in the patient.

Figure 1:
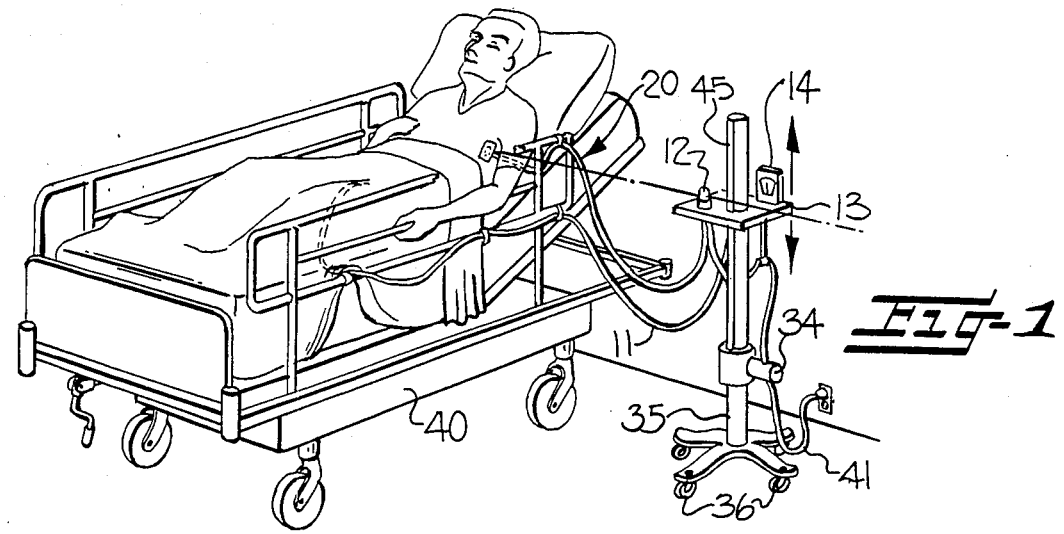
FIG. 1 is a perspective view of a patient in a hospital bed and illustrating the present automatic leveling device positioned adjacent the bed and connected to the patient.

The motive means also includes a reversible motor 34 electrically connected to the up and down switch 33 which is maintained in a fixed position on the housing of a stand 35, which may be similar to the usual type of intravenous infusion pole stand. The stand 35 is provided with rollers or casters 36 to facilitate rolling movement of the same relative to a hospital bed 40 on which the patient is positioned in a normally reclining position. The hospital bed 40 is adjustable vertically as well as being adjustable to raise and lower the head and/or feet and legs of the patient. As illustrated in FIG. 1, the reversible motor 34 is connected to a suitable power source, such as a wall outlet, by wires 41. However, the reversible motor 34 can also be provided with a battery pack as an alternate source of power, if desired.

The reversible motor 34 is provided with an output power shaft having a worm 42 fixed thereto and in driving engagement with a worm gear 43 which is fixed on the lower end of a vertically extending threaded shaft or rod 44. The upper and lower ends of the threaded rod 34 are suitably journaled in a vertically extending tubular portion 45 of the stand 35. An internally threaded bushing 46 is supported on the threaded rod 44 and in turn supports the table 13 so that rotation of the threaded rod 44 in one direction will raise the table 13 and rotation in the opposite direction will lower the same.

Operation

After the pressure catheter 10 is implanted in the patient, the attendant attaches the patient end of the liquid level tube means 20 to the body of the patient at the same level as the catheter 10 is implanted in the patient so that the patient end of the liquid level tube means 20 will be raised and lowered as the patient is raised and lowered along with the pressure catheter 10. If the level of the mercury 23 adjacent the automatic leveling end of the liquid level tube means 20 is at the level indicated in FIG. 3, that is in contact with the electrodes 30 and 31, the transducer 12 and the table or platform 13 will be in the proper position to give an accurate reading of the hemodynamic pressure in the body of the patient since it will be vertically aligned with the catheter 10 in the patient.

When the position of the patient is changed, as when the bed 40 is vertically raised or the inclined backrest portion of the bed is lowered or raised, as illustrated in FIG. 1, the level of the mercury 23 in the patient end of the liquid level tube means 20 will be correspondingly lowered or raised. For example, if the backrest portion of the bed 40 is lowered, the level of the mercury 23 in the leveling end of the liquid level tube means 20 will be lowered so that the mercury 23 will no longer contact the electrode 31. The lowering of the level of the mercury 23 will activate the up/down switch 33 to rotate the motor 34 in one direction so that the threaded rod 44 is rotated in a counterclockwise direction in FIG. 2 to automatically lower the table 13 and the transducer 12 until the level of the mercury 23 again makes contact with the electrode 31. At this time, the up/down switch 33 is deactivated to stop rotation of the reversible motor 34 so that the table 13 and the transducer 12 are maintained in vertical alignment with the catheter 10.

If the vertical position of the catheter 10 is raised, as when the patient and/or the bed 40 is raised, the level of the mercury 30 in the leveling end of the liquid level tube means 20 will be raised and the mercury will contact all three electrodes 30, 31 and 32, thereby activating the up/down switch 33. This will cause the reversible motor 34 to rotate and impart rotation in a clockwise direction to the threaded rod 44 so that the table 13 and the transducer 12 will be raised until they are vertically level with the catheter 10. At this time the level of the mercury 23 in the leveling end of the liquid level tube means 20 will have moved downwardly to the position shown in FIG. 3 and out of engagement with electrode 32. The up/down switch 33 will then stop rotation of the reversible motor 34 and the table 13 and the transducer 12 will remain in a level position relative to the catheter 10.

Thus, the automatic leveling device of the present invention operates to automatically maintain the pressure measuring means, the transducer 12, at the same level as the catheter 10 implanted in the patient. The automatic leveling device of the present invention includes motive means which is automatically operable in response to corresponding raising and lowering of the pressure catheter implanted in the patient to correspondingly raise and lower the support means for the pressure measuring means so that accurate pressure readings are always obtained by the hemodynamic pressure measuring and monitoring system. The present automatic leveling device does not require vertical manual adjustment of the pressure measuring means to maintain the same at the same vertical level as the catheter in the patient, as heretofore required, and thereby frees the attendant to pay close attention to the needs of and to constantly monitor the vital signs of the patient.

In the drawings and specification there has been set forth the best mode presently contemplated for the practice of the present invention, and although specific terms are employed, they are used in a generic and descriptive sense only and not for purposes of limitation, the scope of the invention being defined in the claims.

That which is claimed is:

1. In an apparatus adapted for use in measuring and monitoring hemodynamic pressure in the body of a patient and including a pressure catheter adapted to be implanted in a particular location in the body of the patient, a tube containing pressure-transmitting fluid and being connected at one end to said catheter, pressure measuring means connected to the other end of said tube and being operable by pressure sensed by said catheter, and means supporting said pressure measuring means for vertical movement, the combination therewith of automatic leveling means for imparting vertical movement to said means supporting said pressure measuring means and to thereby automatically maintain said pressure measuring means at the same level as said catheter in response to corresponding vertical movement of said catheter adapted to be implanted in the patient, the improvement in said automatic leveling means comprising tube level means containing a liquid, means for connecting one end of said tube level means to the patient at the same level as the catheter adapted to be implanted in the patient, means connecting the opposite end of said tube level means to said vertically movable means supporting said pressure measuring means, sensor means associated with said opposite end of said tube level means and being operable to determine vertical movement of the liquid level in response to vertical movement of said catheter adapted to be implanted in the patient above and below a predetermined level, and motive means automatically operable in response to said sensor means for correspondingly raising and lowering said means supporting said pressure measuring means in response to vertical movement of said catheter adapted to be implanted in the patient.

2. In an apparatus according to claim 1 wherein said liquid in said tube level means comprises electroconductive mercury.

3. In an apparatus according to claim 2 wherein said sensor means comprises three vertically spaced electrodes positioned in said opposite end of said tube means and being engageable by the level of mercury in said tube level means.

4. In an apparatus according to claim 1 wherein said motive means includes a reversible electric motor, and a threaded vertically disposed rod drivingly connected to said reversible electric motor and being rotatable in opposite directions thereby, and including means operatively connecting said pressure measuring supporting means to said vertical threaded rod to thereby impart vertical movement to said pressure measuring supporting means in response to rotation of said threaded rod in opposite directions.

5. In an apparatus according to claim 1 wherein said pressure measuring means comprises a transducer.

6. In an apparatus according to claim 5 wherein said means supporting said transducer for vertical movement comprises a table on which said transducer is fixed.

7. In an apparatus according to claim 6 including a stand on which said vertically movable table is mounted, and including casters supporting said stand for movement adjacent the patient.

8. In an apparatus according to claim 1 wherein said tube level means includes a first tube containing a liquid, and a second tube containing air, and a filter valve connecting corresponding ends of said liquid tube to said air tube.

9. In an apparatus adapted for use in measuring and monitoring hemodynamic pressure in the body of a patient and including a pressure catheter adapted to be implanted in a particular location in the body of the patient, a tube containing pressure-transmitting fluid and being connected at one end to said catheter, pressure measuring means connected to the other end of said tube and being operable by pressure sensed by said catheter, and means supporting said pressure measuring means for vertical movement, the combination therewith of automatic leveling means for imparting vertical movement to said means supporting said pressure measuring means and to thereby automatically maintain said pressure measuring means at the same level as said catheter in response to corresponding vertical movement of said catheter adapted to be implanted in the patient, the improvement in said automatic leveling means comprising tube level means containing electroconductive mercury, means for connecting one end of said tube level means to the patient at the same level as the catheter adapted to be implanted in the patient, means connecting the opposite end of said tube level means to said means supporting said pressure measuring means, vertically spaced electrodes positioned in said opposite end of said tube level means and being operable to sense vertical movement of the mercury level in response to vertical movement of said catheter adapted to be implanted in the patient above and below a predetermined level, and motive means automatically operable in response to contact of the mercury with said electrodes for correspondingly raising and lowering said means supporting said pressure, measuring means in response to vertical movement of said catheter adapted to be implanted in the patient.

* * * * *